(12) United States Patent
Swift

(10) Patent No.: US 11,131,620 B1
(45) Date of Patent: Sep. 28, 2021

(54) METHODS OF BONDING ARTICLES USING MOISTURE-CURING ADHESIVE COMPOSITION

(71) Applicant: Swift IP, LLC, Weston, FL (US)

(72) Inventor: Philip Swift, Weston, FL (US)

(73) Assignee: Swift IP, LLC, Weston, FL (US)

( * ) Notice: Subject to any disclaimer, the term of this patent is extended or adjusted under 35 U.S.C. 154(b) by 250 days.

(21) Appl. No.: 15/857,764

(22) Filed: Dec. 29, 2017

(51) Int. Cl.
*G01N 19/04* (2006.01)
*G01N 33/44* (2006.01)
(Continued)

(52) U.S. Cl.
CPC ............ *G01N 19/04* (2013.01); *B32B 7/12* (2013.01); *B32B 13/04* (2013.01); *B32B 15/043* (2013.01); *B32B 21/02* (2013.01); *B62D 21/00* (2013.01); *C09J 5/04* (2013.01); *G01N 33/44* (2013.01); *A01K 63/00* (2013.01); *B29C 65/484* (2013.01);
(Continued)

(58) Field of Classification Search
CPC .......... G01N 19/00; G01N 19/04; G01N 3/08; G01N 3/14; G01N 2203/0017; G01N 2203/0262; G01N 2203/0264; G01N 2203/0033; G01N 2203/026; G01N 33/44; C09J 175/04; C09J 5/04; F16L 1/26; B32B 7/12; B32B 37/12; B32B 2037/1253; B32B 2037/1261; B32B 13/04; B32B 15/043; B32B 21/02; B32B 21/04; B29C 65/00; B29C 65/48; B29C 65/4805; B29C 65/483; B29C 65/484; B29C 65/52; B29C 65/82; B29C 65/8207; B29C 65/8215; B29C 66/00; B29C 66/001; B29C 66/0012; B29C 66/0016; B29C 66/97; B29C 73/00; B29C 73/02; B29C 73/04; A01K 63/00; B62D 21/00; E04H 2004/146
USPC .... 156/60, 64, 71, 94, 182, 281, 295, 304.1, 156/325, 326, 327, 330.9, 331.1, 331.4; 73/760, 788, 789, 794, 795, 806, 826, 73/827, 830, 834
See application file for complete search history.

(56) References Cited

PUBLICATIONS

Advanced Adhesion Inc. "Mr. Sticky's TV Video," published Jul. 16, 2008; https://www.youtube.com/watch?v=tZ0DN995H1s (Year: 2008).*

(Continued)

*Primary Examiner* — Michael A Tolin
*Assistant Examiner* — Brian R Slawski
(74) *Attorney, Agent, or Firm* — Banner & Witcott, Ltd.

(57) ABSTRACT

An adhesive composition may be applied to a surface, such as plastic, metal, wood, stucco, plaster, brick, concrete, glass, rubber, tile, fiberglass, ceramic, porcelain, canvas, stone, or drywall. The adhesive-containing surface is then pressed into contact with a second surface to create a strong, watertight bond. The methods disclosed herein may be used to assemble and/or repair a variety of articles and structures, such as roofs, gutters, boats, kayaks, personal watercraft, canoes, rafts, inflatable articles such as toys, sporting equipment, and air mattresses, outdoor equipment, mobile homes, recreational vehicles, campers, garden hoses, low-pressure PVC and plumbing pipes, tents, vinyl awnings, covers and tarps, swimming pools, windows, doors, walls, seams, vents, air ducts, HVAC systems, and the like. Also disclosed herein are methods of testing the bonding strength of an adhesive, methods of affecting underwater repairs, and methods of assembling an all-terrain vehicle.

8 Claims, 4 Drawing Sheets

(51) Int. Cl.
*C09J 5/04* (2006.01)
*B32B 7/12* (2006.01)
*B32B 13/04* (2006.01)
*B32B 15/04* (2006.01)
*B62D 21/00* (2006.01)
*B32B 21/02* (2006.01)
*A01K 63/00* (2017.01)
*E04H 4/14* (2006.01)
*B32B 37/12* (2006.01)
*B29C 65/48* (2006.01)
*B29C 65/82* (2006.01)
*B29C 65/00* (2006.01)

(52) U.S. Cl.
CPC ...... *B29C 65/8215* (2013.01); *B29C 66/0016* (2013.01); *B32B 2037/1261* (2013.01); *C09J 2203/00* (2013.01); *E04H 2004/146* (2013.01); *G01N 2203/0033* (2013.01); *G01N 2203/026* (2013.01)

(56) References Cited

PUBLICATIONS

Advanced Adhesion Inc. "Mr Sticky's TV AD 2," published Aug. 15, 2008; https://www.youtube.com/watch?v=5_m-nkHavHU (Year: 2008).*

Advanced Adhesion Inc. "PVC Pipe Glued Underwater," published Mar. 18, 2015; https://www.youtube.com/watch?v=GYbUvWysol8&feature=youtu.be (Year: 2015).*

Profi-Glue Limited. "Underwater Magic / www.underwatermagic.eu," published Dec. 8, 2013; https://www.youtube.com/watch?v=CYxiYam2LPI (Year: 2013).*

Origami Plus. "Origami Chain—Make a Very Strong DIY Paper Chain with only Copy Paper, no Glue and no Tape," published Sep. 8, 2017; https://www.youtube.com/watch?v=iB0hadCVglc (Year: 2017).*

Loctite North America. "How Loctite Pulled a Train Using Only Adhesive," published Jun. 14, 2017; https://www.youtube.com/watch?v=1bSjVFawpqs (Year: 2017).*

The Gorilla Glue Company. "Gorilla Super Glue Truck Lift," published Apr. 9, 2008; https://www.youtube.com/watch?v=3tPxfdK5wtk (Year: 2008).*

Loctite North America. "Loctite Super Glue breaks a World Record!," published May 17, 2011; https://www.youtube.com/watch?v=2tfo98Ansxo (Year: 2011).*

Purdue University, College of Engineering (Purdue Engineering). "Biomimetic Underwater Glue," published Mar. 9, 2017; https://www.youtube.com/watch?v=rhblikR3SBU (Year: 2017).*

Science Channel (Street Science). "Think Super Glue Can Lift A Pickup Truck?," Science Channel, Street Science, published Dec. 22, 2017; https://www.youtube.com/watch?v=U7deOOmrxBM (Year: 2017).*

Mitutoyo Corp. "The History of Gauge Blocks," Catalog No. E12016, 2013; https://www.mitutoyo.co.jp/eng/support/service/catalog/09/E12016.pdf#:~:text=The%20first%20time%20Mitutoyo%20made%20sales%20of%20gauge,is%20essential%20to%20the%20production%20of%20gauge%20blocks. (Year: 2013).*

* cited by examiner

METHODS OF BONDING ARTICLES USING MOISTURE-CURING ADHESIVE COMPOSITION

BACKGROUND

Aerosol-propelled rubber compositions, such as FLEX SEAL®, and viscous liquid rubber compositions, such as FLEX SEAL® LIQUID, sold by Swift Response LLC, have been widely popular for consumer use in waterproofing and repairing various articles and structures. It would be desirable to develop alternative techniques for bonding and/or repairing household articles, motor vehicles, structures, and the like, such as for purposes of assembly and/or repair. It would be particularly desirable to develop techniques which are safe and easy-to-use for consumers.

SUMMARY

Aspects of the invention involve techniques in which an adhesive composition is applied to a surface, such as plastic, metal, wood, stucco, plaster, brick, concrete, glass, rubber, tile, fiberglass, ceramic, porcelain, canvas, stone, or drywall. The adhesive-containing surface is then pressed into contact with a second surface to create a strong, watertight bond. The methods disclosed herein may be used to assemble and/or repair a variety of articles and structures, such as roofs, gutters, boats, kayaks, personal watercraft, canoes, rafts, inflatable articles such as toys, sporting equipment, and air mattresses, outdoor equipment, mobile homes, recreational vehicles, campers, garden hoses, low-pressure PVC and plumbing pipes, tents, vinyl awnings, covers and tarps, above-ground swimming pools, windows, doors, walls, seams, vents, air ducts, HVAC systems, and the like.

In one example embodiment, a method of testing the bond strength of an adhesive is provided. An adhesive composition may be applied to a first surface of a first block, such as a brick, cinderblock, wooden block, or metal block. The first surface of the first block, containing the adhesive, may be brought into contact with a second surface. The second surface may be a surface of a second block of similar or dissimilar construction to that of the first block, or a structural member such as a horizontally disposed steel or wooden beam. In some examples, one or more additional blocks may be bonded to the assembly in a similar manner, e.g., to create a bonded stack of 3, 4, 5, or more blocks. Bond strength of the assembly may be tested by holding one of the blocks (e.g., by hand or with the aid of a tool such as a clamp) and allowing the bonded block(s) to be suspended beneath the held block. In the case where the second surface is a structural member, the first block may be bonded to an underside of the structural member such that the first block is suspended from the structural member. A successful test may be characterized by the suspended block(s) remaining bonded to the adjacent surface despite the weight of the suspended block(s).

In another illustrative embodiment, a method of testing bond strength of an adhesive comprises applying an adhesive composition to a first surface of a first block, such as a brick, cinderblock, wooden block, or metal block. The first surface of the first block containing the adhesive may be brought into contact with a second surface of a second block of similar or dissimilar construction to the first block. A weight may be attached to the first block or the second block. The bonded assembly, along with the attached weight, may be suspended from a support. A successful test may be characterized by the first and second blocks remaining bonded together notwithstanding the mass of the weight attached to the second block. In some examples, the adhesive is allowed to cure, e.g., for a period of 4-7 days, to attain greater adhesive strength thereby allowing a significant amount of weight (e.g., 500 to 1,000 lbs.) to be suspended from the bonded assembly without delamination.

In another illustrative embodiment, a method of affecting underwater repairs is provided. An adhesive composition may be applied to a first surface. The first surface containing the adhesive may be brought into contact with a second surface that is underwater. In some examples, the first surface also may be underwater at the time that the adhesive is applied thereto. The first surface and the second surface may be pressed together to bond the first surface to the second surface to affect the underwater repair.

In yet another illustrative embodiment, a method of assembling an all-terrain vehicle is provided. The method includes a step of applying an adhesive composition to a portion of a first frame member and bonding the first frame member to a second frame member.

Successive frame members are bonded to each other to complete the assembly, wherein at least the entire frame of the all-terrain vehicle is joined together using only the adhesive, thereby avoiding the need for the use of welding or other assembly techniques. In some examples, the thus-assembled all-terrain vehicle may be operated over uneven terrain whereupon the all-terrain vehicle remains intact.

BRIEF DESCRIPTION OF THE DRAWINGS

A more complete understanding of the present invention and certain advantages thereof may be acquired by referring to the following detailed description in consideration with the accompanying drawings, in which.

DETAILED DESCRIPTION

A polymer-based, construction-quality adhesive composition (sometimes referred to herein as "adhesive" or "adhesive composition") may be applied to a surface such as roofs, gutters, boats, kayaks, personal watercraft, canoes, rafts, inflatable articles such as toys, sporting equipment, and air mattresses, outdoor equipment, mobile homes, motor vehicles, campers, garden hoses, low pressure PVC and plumbing pipes, tents, vinyl awnings, covers and tarps, above-ground swimming pools, windows, doors, walls, seams, vents, air ducts, HVAC systems, furniture, and the like. The adhesive-containing surface then may be pressed into contact with a second surface to create a watertight bond, such as for purposes of repair and/or assembly.

The adhesive should highly flexible when applied, allowing it to readily conform to the shape of the article to which it is applied. The adhesive may form a strong bond with a variety of surfaces under a variety of conditions. In some examples, the adhesive may be applied to a surface while in contact with water, so that structures such as aquariums, swimming pools, hot tubs, ponds, vessels, and docks may be repaired underwater. In some examples, the adhesive may be supplied in a tube that may be squeezed to easily apply a quantity of the adhesive onto a surface. If desired, the adhesive may be provided in a receptacle that allows it to be dispensed with the aid of a tool such as a caulk gun.

The particular type of adhesive used is not limited provided that it has sufficiently high adhesive strength and water-resistant properties. A number of suitable adhesive compositions are commercially available, including polyurethane construction adhesives, polyurethane based moisture-curing adhesives, silane modified polymers, and elastomers. Other types of adhesives may be based, for example, on silicone, epoxy, acrylate, or synthetic rubber. In one example, a rapid polymerizing, one-part moisture-curing hybrid material may be used. In some examples, the adhesive contains no solvent or water and is VOC compliant. The adhesive may be formulated in a variety of colors tailored to particular applications or consumer preferences. For example, adhesive compositions may be clear, white, off-white, black, gray, blue, green, red, almond, brown, silver, yellow, terra cotta, or other suitable color. The selection of appropriate pigment(s) or other colorant(s) needed to achieve a desired color will be apparent to persons skilled in the art with the aid of no more than routine experimentation.

Figure 1A:
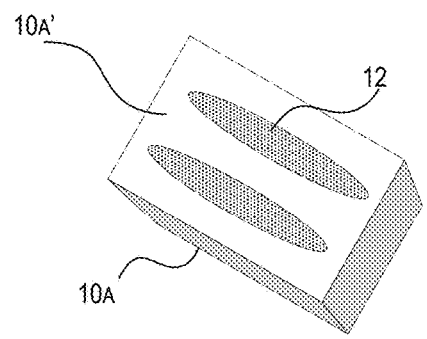
FIGS. 1A-1D schematically illustrate methods of bonding blocks and testing the resulting bond strength in accordance with one or more illustrative aspects.
Figure 1B:
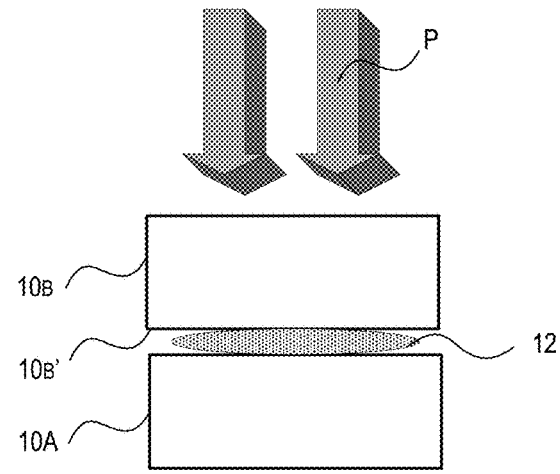
Figure 1C:
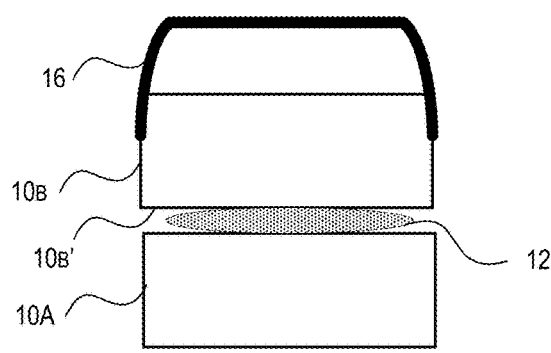
Figure 1D:
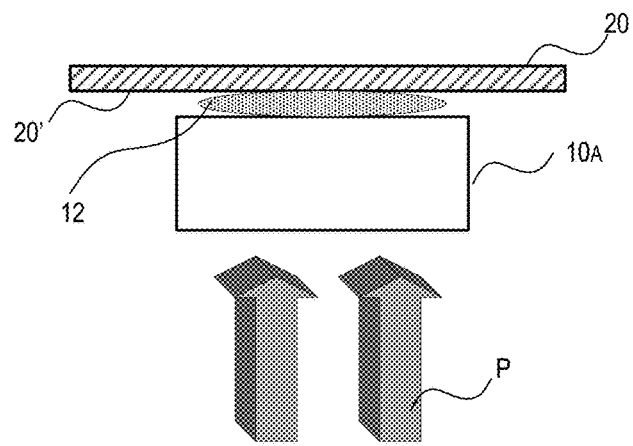

FIGS. 1A-1D show methods of testing the bond strength of an adhesive in accordance with some illustrative aspects. As shown in FIG. 1A, an adhesive composition 12 may be applied to a first surface 10a' of a first block 10a, such as a brick, cinderblock, wooden block, or metal block. As shown in FIG. 1B, the first surface 10a' of the first block 10a which contains the adhesive 12 may be brought into contact with a second surface 10b'. The second surface may be a surface 10b' of a second block 10b of similar or dissimilar construction to that of the first block 10a, as shown in FIG. 1B, or alternatively a surface 20' of a structural member 20 such as a horizontally disposed steel or wooden beam, as shown in FIG. 1D. Pressure P may be applied to affect bonding between the first surface 10a' and the second surface 10b' or 20'. In some examples (not illustrated), one or more additional blocks may be bonded to the assembly in a similar manner, e.g., to create a bonded stack of 3, 4, 5, or more blocks. Bond strength of the assembly may be tested by holding one of the blocks (e.g., by hand or with the aid of a tool such as a clamp 16) and allowing the bonded block(s) to be suspended beneath the held block. In the case where the second surface is a structural member, the first block may be bonded to an underside of the structural member such that the first block is suspended from the structural member, as depicted in FIG. 1D. A successful test may be characterized by the suspended block(s) remaining bonded to the adjacent surface despite the weight of the one or more suspended block(s).

Figure 2:
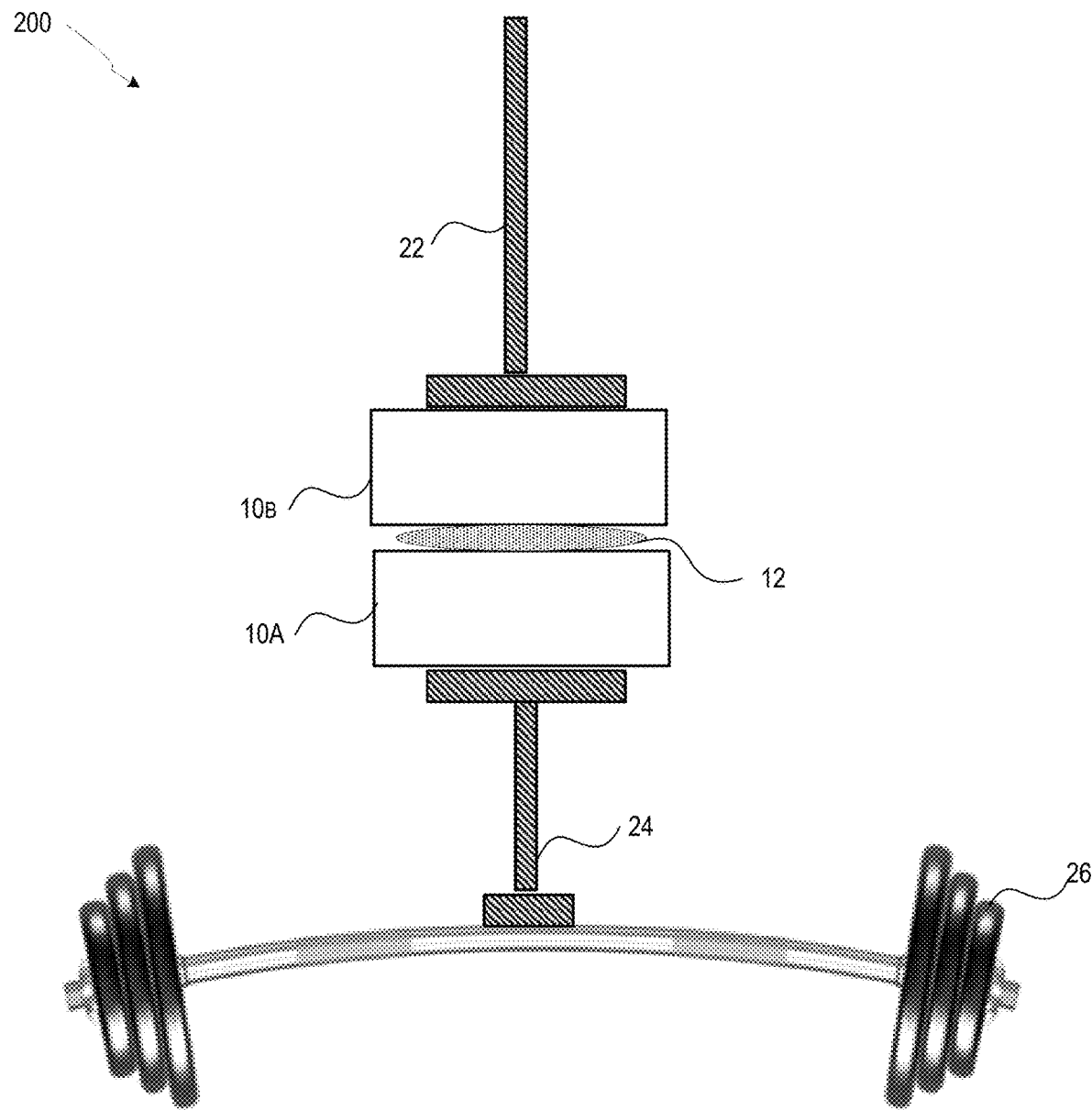
FIG. 2 schematically illustrates a method of testing bond strength in accordance with another illustrative aspect.

FIG. 2 shows another illustrative embodiment of testing the bond strength of an adhesive. An adhesive composition may be used to bond a first block 10a to a second surface in a similar manner to that which was previously described. The second surface may be that of a second block 10b, as shown in FIG. 2, or alternatively a structural member 20 as in FIG. 1D. A lower support, such as a metal bracket 24, may be attached to the first block 10a and a weight 26 may be attached to the lower support 24. The bonded assembly, along with the attached weight 26, may be suspended from an upper support 22, such as a metal bracket and/or cable. A successful test may be characterized by the first 10a and second 10b blocks remaining bonded together notwithstanding the mass of the weight 26 being supported by the bonded assembly. In some examples, the adhesive may be allowed to cure, e.g., for a period of 4-7 days, to attain greater adhesive strength. When the adhesive reaches these greater adhesive strengths, a significant amount of weight (e.g., 500 to 1,000 lbs. or more) may be suspended from the bonded assembly without causing delamination.

Figure 3A:
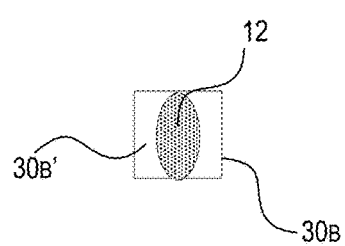
FIGS. 3A-3E schematically illustrate methods of making underwater repairs in accordance with additional illustrative aspects.
Figure 3C:
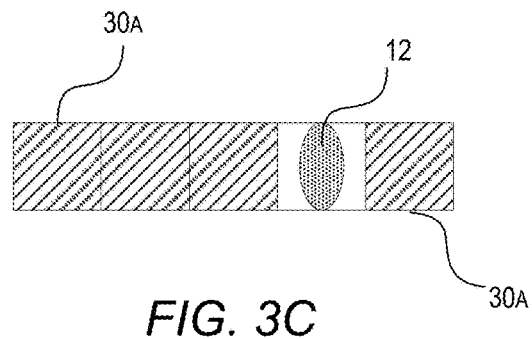
Figure 3B:
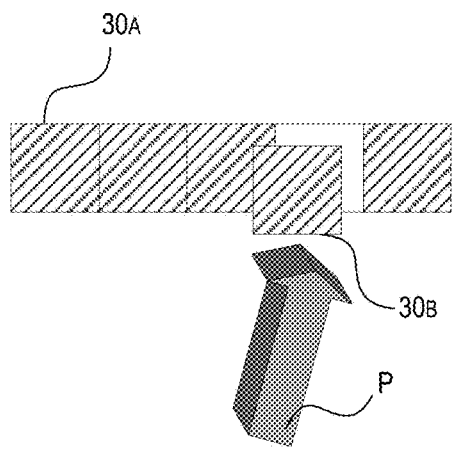
Figure 3D:
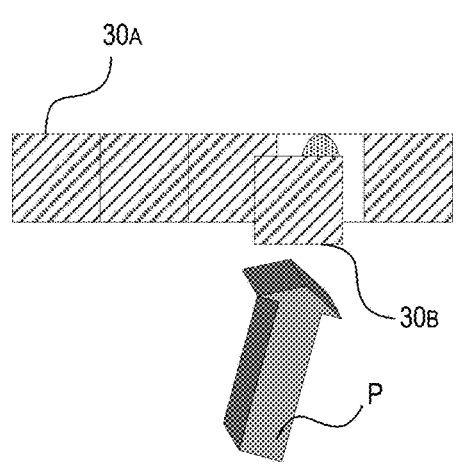
Figure 3E:
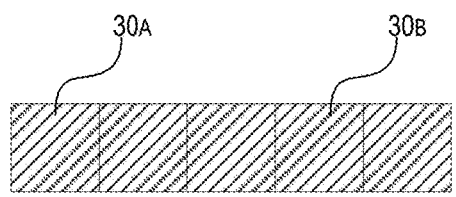

FIGS. 3A-3E show methods of affecting underwater repairs in accordance with additional illustrative embodiments. As shown in FIG. 3A, an adhesive composition 12 may be applied to a first surface, such as the rear surface 30b' of a ceramic tile 30b. The first surface 30b' containing the adhesive 12 may be brought into contact with a second surface that is underwater. For example, as shown in FIG. 3B, the tile 30b may be bonded in a space adjacent to existing tiles 30a. In some examples, the first surface also may be underwater at the time that the adhesive is applied thereto. For example, FIG. 3C illustrates applying adhesive 12 to an underwater surface for receiving a tile 30b. The tile 30b may be pressed P into place so that the adhesive 12 bonds the tile 30b to the second surface to affect the underwater repair. The repaired underwater structure is shown in FIG. 3E. Various other types of materials, e.g., wood, metal, ceramic, and the like, may be bonded to appropriate surfaces using the adhesive to affect underwater repairs of various structures, such as vessels, docks, pools, ponds, spas, and the like.

Figure 4:
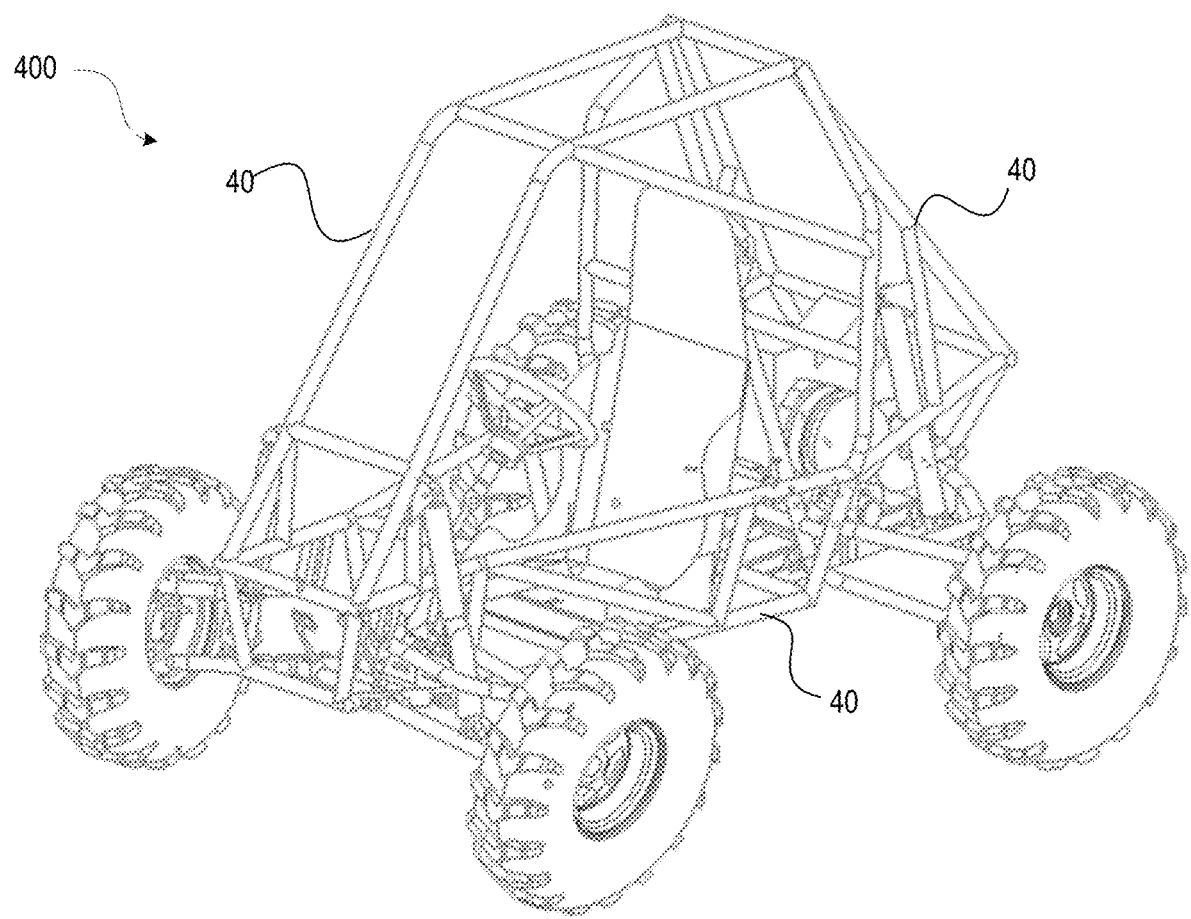
FIG. 4 schematically illustrates a method of assembling an all-terrain vehicle in accordance with another illustrative aspect.

FIG. 4 depicts a method of assembling an all-terrain vehicle 400 in accordance with another illustrative embodiment. A plurality of frame members 40 may be joined by applying an adhesive composition to an end portion of a frame member 40 and pressing it into contact with an adjacent frame member 40. Successive frame members 40 may be bonded together in a similar manner to complete the frame assembly, as shown in FIG. 4. At least the entire frame of the all-terrain vehicle 400 may be joined together using only the adhesive, thereby avoiding the need for the use of welding or other assembly techniques. The remaining components of the vehicle 400 such as the motor, wheels, axles, steering assembly, suspension, seat, steering wheel, and operating controls may be secured to the assembled frame and/or to other vehicle components. In some examples, the thus-assembled vehicle 400 may be driven by an operator over uneven terrain, which may include obstructions such as rocks and logs, and yet the frame and vehicle remain intact due to the strength of the adhesive bonds.

The adhesive composition may be used to affect various other household repairs. For examples, the adhesive may be applied to an upper surface of a table base, and a tabletop may be placed on top of the table base to secure the tabletop to the table base. In other examples, adhesive may be applied to a gutter or drain spout to bond the gutter or drain spout to a fitting or to another conduit. In other examples, the adhesive may be applied to frame for a ceiling light fixture to create a watertight seal between the frame and a ceiling. The adhesive also may be applied to various types of building materials such as drywall, wood, stone or ceramic tile, vinyl siding, and the like to install and/or repair sections of such materials.

The foregoing description should be considered illustrative rather than limiting. It should be recognized that various modifications can be made without departing from the spirit or scope of the invention as described and claimed herein.

What is claimed is:

1. A method of testing the bond strength of an adhesive composition comprising:

applying the adhesive composition to a first surface of a first block, wherein a lower support is attached to the first block, and wherein the lower support is a metal bracket and the first block is wooden;

bringing the first surface of the first block into contact with a second surface to form a bond between the first surface and the second surface;

allowing the adhesive composition to cure for a period of at least 4 days;

suspending the first block from the second surface; and suspending a barbell weight from the lower support, whereupon the first block remains bonded to the second surface.

2. The method of claim 1, wherein the adhesive composition is applied to the first surface while the first surface is underwater.

3. The method of claim 1, wherein the second surface is a surface of a second block selected from the group consisting of a brick, cinderblock, wooden block, and metal block.

4. The method of claim 3, further comprising applying the adhesive composition to a third surface and bringing the third surface into contact with an exposed surface of the second block, wherein the exposed surface of the second block is positioned on an underside of the second surface of the second block; and suspending the first block and the second block from the third surface whereupon the first block and the second block remain bonded to the second surface and third surface, respectively.

5. The method of claim 1, wherein the second surface comprises a surface of a horizontally disposed steel or wooden beam, and wherein the disposed steel or wooden beam is a structural member, and wherein the first block is bonded to an underside of the structural member such that the first block is suspended from the structural member.

6. The method of claim 1, wherein the barbell weight weighs at least 500 lbs.

7. The method of claim 1, wherein the barbell weight weighs at least 1,000 lbs.

8. The method of claim 1, further comprising an upper support attached to the second surface, wherein the upper support is a metal bracket and the second surface is a surface of a second wooden block.

\* \* \* \* \*